(12) United States Patent
Suter et al.

(10) Patent No.: US 7,097,842 B2
(45) Date of Patent: *Aug. 29, 2006

(54) MODIFIED VACCINIA VIRUS ANKARA FOR THE VACCINATION OF NEONATES

(75) Inventors: Mark Suter, Luzern (CH); Sabine Vollstedt, Zurich (CH); Paul Chaplin, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 60 days.

This patent is subject to a terminal disclaimer.

(21) Appl. No.: 10/418,854

(22) Filed: Apr. 18, 2003

(65) Prior Publication Data

US 2003/0224018 A1 Dec. 4, 2003

Related U.S. Application Data

(63) Continuation-in-part of application No. PCT/EP01/13628, filed on Nov. 22, 2001.

(30) Foreign Application Priority Data

Nov. 23, 2000 (DK) .............................. 2000 01764
Apr. 19, 2002 (DK) .............................. 2002 00590

(51) Int. Cl.
- A61K 39/285 (2006.01)
- C12N 7/00 (2006.01)
- C12N 7/01 (2006.01)
- C12N 7/04 (2006.01)
- C12N 15/863 (2006.01)

(52) U.S. Cl. .............................. 424/199.1; 424/232.1; 424/93.2; 424/93.6; 435/235.1; 435/236; 435/320.1

(58) Field of Classification Search ............. 424/199.1, 424/232.1, 93.2, 93.6, 281.1; 435/235.1, 435/236, 320.1
See application file for complete search history.

(56) References Cited

U.S. PATENT DOCUMENTS

| | | | |
|---|---|---|---|
| 3,914,408 A | 10/1975 | Mebus | |
| 4,191,745 A | 3/1980 | Mayr et al. | |
| 5,338,683 A | 8/1994 | Paoletti et al. | |
| 5,770,212 A * | 6/1998 | Falkner et al. | 424/199.1 |
| 5,843,456 A * | 12/1998 | Paoletti et al. | 424/199.1 |
| 6,204,250 B1 | 3/2001 | Bot et al. | |
| 6,605,465 B1 * | 8/2003 | Paoletti | 435/320.1 |
| 6,685,950 B1 | 2/2004 | Weber et al. | |
| 6,761,893 B1 * | 7/2004 | Chaplin et al. | 424/199.1 |
| 6,805,870 B1 | 10/2004 | Mayr et al. | |

FOREIGN PATENT DOCUMENTS

| | | | |
|---|---|---|---|
| WO | 90/12882 | | 11/1990 |
| WO | 95/22978 | | 8/1995 |
| WO | WO 95/22978 | * | 8/1995 |
| WO | WO 97/31119 | | 8/1997 |
| WO | 98/17283 | | 4/1998 |
| WO | 01/68820 | | 9/2001 |
| WO | WO 01/68820 | | 9/2001 |
| WO | 02/42480 | | 5/2002 |
| WO | WO 02/42480 | | 5/2002 |

OTHER PUBLICATIONS

Watts et al (Nature Medicine 5:427-430, 1999).*
Siegrist (Vaccine 19 :3331-3346, 2001).*
Siegrist et al (Vaccine 16: 1473-1478, 1998).*
Suarez et al (Obstetrics & Gynecology 100:87-93, Jul. 2002).*
Zhu et al (Virology 276:202-213, 2000).*
Roberts (Drug Discovery Today 7:936-937, 2002).*
Monteil et al (Journal of General Virology 78:3303-3310, 1997).*
Siegrist (Vaccine 19:3331-3346, 2001; International Reviews of Immunology 19:195-219, 2000.*
Yong-de-Zhu, et al.; Virology 276, 202-213 (2000); Evaluation of Recombinant Vaccinia Virus—Measles Vaccines in Infant Rhesus Macaques with Preexisting Measles Antibody.
Jiri Kovarik, et al.; Virology 285, 12-20 (2001); Induction of Adult-like Antibody, Th1, and CTL Responses to Measles Hemagglutinin by Early Life Murine Immunization with An Attenuated Vaccinia-Derived NYVAC(K1L) Viral Vector.
Gilles Dadaglio, et al.; The Journal of Immunology 168, 2219-2224 (2002); Efficient In Vivo Priming of Specific Cytotoxic T Cell Responses by Neonatal Dendritic Cells.

(Continued)

*Primary Examiner*—Mary E. Mosher
(74) *Attorney, Agent, or Firm*—Hueschen and Sage

(57) ABSTRACT

The invention concerns the use of a virus for the preparation of a medicament for the vaccination, treatment, or protection, of a neonatal or prenatal animal, including a human, wherein the virus is capable of infecting the cells of the neonatal or prenatal animal, including a human, but not capable of being replicated to infectious progeny virus in the neonatal or prenatal animal, including a human. The virus is preferably a Modified Vaccinia Virus Ankara.

Figure 1A:
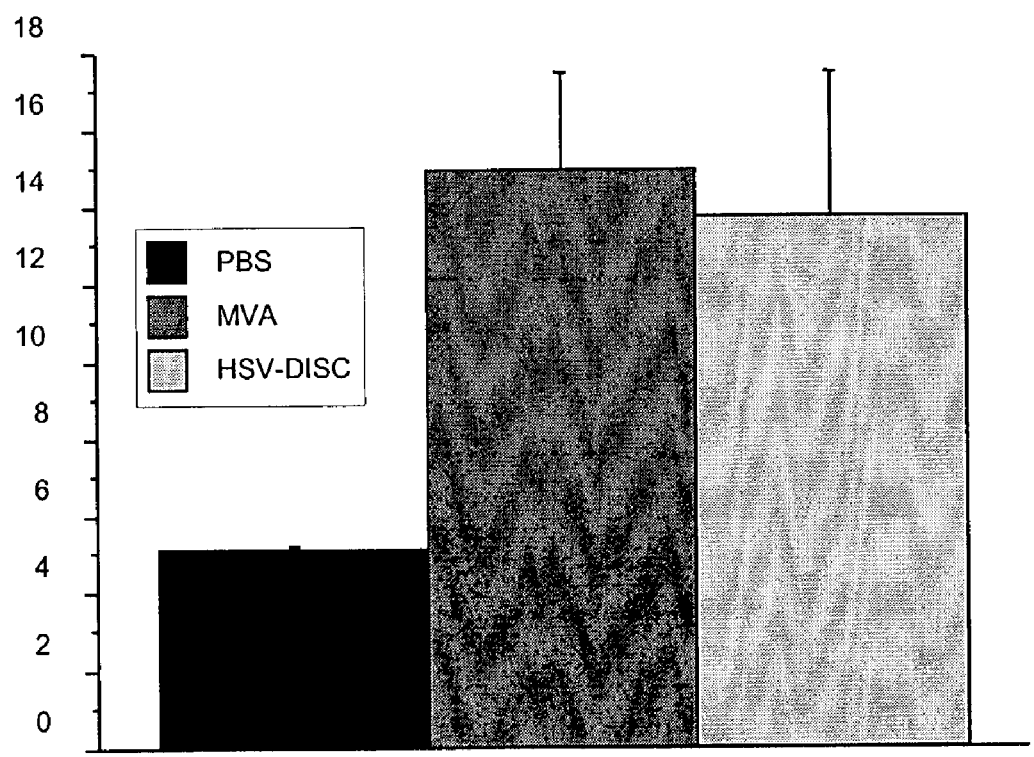

In particular, the invention concerns the vaccination of neonates against infections with viruses belonging the same virus group as the virus used for vaccination. Moreover, the invention concerns the vaccination of neonates against antigens selected from foreign antigens and tumor antigens, wherein the tumor antigen and/or the foreign antigen are different from the antigens associated with the virus. The invention further concerns the use of viruses as defined above to (i) increase the level of factors which activate dendritic cells or their precursor cells, (ii) and/or to increase the number of dendritic cells or their precursor cells, (iii) and/or to increase the production and/or cellular content of an interferon (IFN) or IL-12.

26 Claims, 8 Drawing Sheets

OTHER PUBLICATIONS

John Paul Ridge, et al.; Science 271, 1723-1726 (Mar. 22, 1996); Neonatal Tolerance Revisited: Turning on Newborn T Cells with Dendritic Cells.

B. Vilsmeier, Paraimmunity inducing effects of vaccinia strain MVA. (1999) Berl. Münch. Tierärztl. Wschr. 112:329-333.

A. Mayr, Paraspezifische Vaccinen aus Pockenviren (Paramunitätsinducer): eine neue Art von Impfstoff (1999) Ärztezeitschrift für Naturheilverfahren 40, 8 pp. 550-557.

M. Franchini, et al., Protective T-Cell-Based Imminity Induced in Neonatal Mice by a Single Replicative Cycle of Herpes Simplex Virus. (2001) Journal of Virology 75:83-89.

K. Stittelaar, et al. Protective Immunity in Macaques Vaccinated with a Modified Vaccinia Virus Ankara-Based Measles Virus Vaccine in the Presence of Passively Acquired Antibodies. (2000) Journal of Virology 74:4236-4243.

A. Mayr Zbl. Vet. Med. B, TC marker of the attenuated vaccinia vaccide strain "MVA" in human cell cultures and protective immunization against orthopox diseases in animals. (1976) 23:417-430.

A. Bot, et al. Induction of immunological memory in baboons primed with DNA vaccine as neonates. (2001) Vaccine 19:1960-70 (Abstract only).

C. McLean, et al. Induction of a protective immune response by mucosal vaccination with a DISC HSV-1 vaccine. (1996) Vaccine 14:987-92, (Abstract only).

M. Monteil, et al. Effective priming of neonates born to immune dams against the immunogenic pseudorabies virus glycoprotein gD by replication-incompetent adenovirus-mediated gene transfer at birth. (1997) Journal of General Virology 78:3303-10.

C. Siegrist Vacciniation in the neonatal period and early infancy. (2000) Int. Rev Immunol. 19:195-219, (Abstract only).

I. Belyakov, et al. Shared modes of protection against poxvirus infection by attenuated and conventional smallpox vaccine viruses, (2003) Proc. Natl. Acad. Sci. USA 100:9458-63.

Centers for Disease Control and Prevention (CDC) "Smallpox Fact Sheet" (2003).

B. Vilsmeier, Berl. Munch. Tierarztl. Wochenschrift 112, 329-333 (1999).

*MVA-BN: A safe and efficacious smallpox vaccine option.* Advances in Life Science Feb. 2, 2002, http://www.advancesinlifescience.com/management_2.htm.

Roduit, et al. Immunogenicity and Protective Efficacy of Neonatal Vaccination against *Bordetella pertussis* in a Munine Model: Evidence for Early Control of Pertussis. Infection and Immunity, Jul. 2002, p. 3521-3528.

*Engerix®-B Leaflet of May 9, 2005*, GlaxoSmithKline Biologicals SA.

Moss, B. (1996) Geneically engineered poxviruses for recombinant gene expression, vaccination, and safety. Proc. Natl. Acad. Sci. USA 93:11341-11348.

Stittelaar, et al. (2000) Protective Immunity in Macaques Vaccinated with a Modified Vaccinia Virus Andara-Based Measles Virus Vaccine in the Presence of Passively Acquired Antibodies. Journal of Virology 74:4236-4243.

International Preliminary Examination Report, dated Jan. 11, 2006, four (4) pages.

Tartaglia, et al. "NYVAC: a highly attenuated stratin of vaccinia virus" Virology 1992, vol. 188, pp. 217-232.

Kovarik, et al. "Induction of adult-like antibody, Th1, and CTL responses to measles hemagglutinin by early life murine immunization with an attenuated vaccinia-derived NYVAC (K1L) viral vector" Virology Jun. 20, 2001, vol. 285, pp. 12-20.

Kazanji, et al. "Immunogenicity and protective efficacy of recombinant human T-cell leukaemia/lymphoma virus type 1 NYVAC and naked DNA vaccine candidates in squirrel monkeys (*Saimiri sciureus*)" Journal of Virology, Jul. 2001, vol. 75(13), pp. 5939-5948.

\* cited by examiner

Figure 2:

CD11c cells in 2 w old mice after MVA treatment

| Experiment BN9 | n | blood | | spleen | |
|---|---|---|---|---|---|
| | | % CD11c | % CD11c CD8 | % CD11c | % CD11c CD8 |
| naïve | 3 | 3.5 | 0.4 | 4.9 | 1.3 |
| 1 Vaccination at birth | 3 | 7.4 | 2.1 | 16.1 | 2.0 |
| 1 vaccination at d7 | 4 | 21.5 | 17.0 | 4.4 | 17.6 |
| 2 vaccination d 0 and 7 | 4 | 42.7 | 35.6 | 27.9 | 25.7 |

Figure 5:

9 challenge experiments with HSV-1

|  | infected | survivors |
|---|---|---|
| Controls | 45 | 0 |
| MVA | 40 | 34 |

MODIFIED VACCINIA VIRUS ANKARA FOR THE VACCINATION OF NEONATES

The invention concerns the use of a virus for the preparation of a medicament for the vaccination or treatment of a neonatal or prenatal animal, including a human, wherein the virus is capable of infecting the cells of the neonatal or prenatal animal, including a human, but not capable of being replicated to infectious progeny virus in the neonatal or prenatal animal, including a human. The virus is preferably a Modified Vaccinia Virus Ankara.

In particular, the invention concerns the vaccination of neonates against infections with viruses belonging to the same virus group as the virus used for vaccination. Moreover, the invention concerns the vaccination of neonates against antigens selected from foreign antigens and tumor antigens, wherein the tumor antigen and/or the foreign antigen are different from the antigens associated with the virus. The invention further concerns the use of viruses as defined above to (i) increase the level of factors which activate dendritic cells or their precursor cells; (ii) and/or to increase the number of dendritic cells or their precursor cells; (iii) and/or to increase the production and/or cellular content of an interferon (IFN) or IL-12.

BACKGROUND OF THE INVENTION

The natural environment of animals and human beings contains a large variety of infectious agents such as viruses, bacteria or fungi. Many of these infectious agents may cause diseases in the infected hosts. Under normal circumstances the infected host recovers from the disease induced by the infectious agent after a certain period of time. This recovery is due to the immune system of an animal, including a human being.

The immune system is the part of the human or animal body that is responsible for eliminating the infectious agent. The immune response is divided into a specific and an unspecific (innate) reaction, although both cooperate closely. The unspecific immune response is the immediate defense against a wide variety of foreign substances and infectious agents. In the innate immune response against viruses, Interferons (IFN)-α and IFN-β are absolutely essential to control initial virus replication and to activate natural killer (NK) cells for immediate destruction of infected cells. Intracellular bacterial or parasitic pathogens induce IL-12 that up regulates IFN-γ in NK cells and/or some T cell subsets. IFN-γ activated NK cells can kill intracellular pathogens. Moreover, IFN-γ also activates macrophages and enables them to kill internalized pathogens.

By far, the richest source of IFN-α/β on a per cell basis are dendritic cells (DC); a specialized cell population strategically distributed throughout the body. Plasmocytoid DC or CD11c$^+$ CD8$^+$ DC are among the best producers of IFN-α/β. CD8$^+$ DC infected with intracellular non-viral pathogens are crucial cells able to secrete IL-12, which is essential in the early steps of immune defense.

A specific immune response can be induced against a particular foreign substance (antigen) after a lag phase, when the organism is challenged with this substance for the first time. Initiation of a specific immune response is also coordinated by DC. There is a constant traffic of these cells from the periphery to the secondary lymphoid organs, the lymph nodes, or spleen where naive T and B cells recirculate. Antigen that is carried by DC to these organs enables activation of naive T- and B cells to become effector T- and B cells. For this, DC not only carry the antigen, but in addition, the plasticity of pathogen recognition allows different gene activation in DC and thus, a pathogen adjusted priming of T cells.

The specific immune response is highly efficient and is responsible for the fact that an individual who recovers from a specific infection is protected against this specific infection. Thus, a second infection with the same, or a very similar, infectious agent causes much milder symptoms, or no symptoms at all, since there is already a "pre-existing specific immunity" to this agent. Such immunity and immunological memory persist for a long time; in some cases, even a lifetime. Accordingly, the induction of an immunological memory can be used for vaccination, i.e. to protect an individual against infection with a specific pathogen.

For vaccination, the immune system is challenged with a vaccine that is less harmful than the pathogenic agent against which an immune response is to be induced. The vaccine comprises or expresses epitopes that are found in, or expressed by, the agent against which the vaccination is done. The organism, thus, is immunized against the agent containing the epitope that is part of the vaccine.

Typical vaccines are attenuated or inactivated viruses (e.g. the polio or small poxyirus vaccines), recombinant proteins (e.g. recombinant Hepatitis B virus S-protein), heat inactivated bacterial toxins (e.g., *Clostridium tetani* toxin), or polysaccharides of the bacterial capsule wall (e.g., *Streptococcus pneumoniae*).

Since infectious diseases may lead to critical conditions in newborns and sucklings, there is an interest in vaccinating children and/or newborn animals as early as possible. Examples of conditions against which a vaccination is desirable are poxyirus infections, including smallpox. Attempts to successfully vaccinate newborns, however, are hampered because the immune system of newborn mammals is not yet mature. The immune system of neonatal infants and mammalian animals is thought to mature gradually over a certain period of time. For humans this maturation occurs during the first year of life. This is the reason why the neonatal age group is left open to various infections during this first year (Gans et al., J. Am. Med. Assoc. (1998) 280, 527–532). More particularly, neonatal infants have impaired B-cell function, deficiencies in primary antigen presentation by dendritic cells, and limited T-cell proliferation (Gans et al., J. Am. Med. Assoc. (1998) 280, 527–532). Shortly after birth, the levels of T cells in the spleen are 1,000 fold lower than in adults. In order to achieve at least a weak immunization, it has been suggested to use either replicating viruses, or formulations comprising an adjuvant, for immunization. However, with replication viruses there is always a risk that the immature immune system may become overwhelmed by viral infection or live viral vaccines, since T cells are necessary for viral clearance (Hassett et al., J. Virol. (1997) 71,7881–7888). Since there is a reduced production of cytokines by Th-1 helper T cells in neonates, the response in infants is predominantly Th-2. Consequently, cytotoxic T cells are not recruited and viral clearance is not achieved.

The situation in mammalian animals is very similar to the situation in humans, i.e.

the immune system after birth is not yet mature. In newborn mice, the number of splenic CD4+ T cells and CD8+ T cells is respectively, 80,000-fold and 1,000-fold lower, than in spleen cells of adults. Moreover, the interferon (IFN) producing system is immature in these mice. Therefore, IFN in neonatal mice is unable to efficiently control the expansion of intracellular pathogens at the site of infection. In addition, the low number and possibly inadequate activation stage of immune cells are too limited to cope with the rapidly expanding pathogens or replicating viruses used for vaccination.

Due to the risk associated with live viral vaccines, it is not recommended to vaccinate neonatal animals, including humans, with replicating viruses. For example, it is not recommended to vaccinate newborns against smallpox with the vaccinia virus strains that had been used up until the eradication of smallpox, i.e., strains such as Elstree, Copenhagen and NYCBH. According to recent recommendations in the USA, babies younger than 12 months of age should not receive the smallpox vaccines commercialized thus far.

The vaccination of neonates with formulations comprising an adjuvant has the disadvantage of introducing numerous harmful substances into the body. Thus, vaccination in human neonates is only done in emergency cases, e.g. in Hepatitis B virus infection.

In summary, it is to be noted that the immune system is not mature at birth. Since vaccination with replication competent viruses or formulations comprising an adjuvant have significant disadvantages; infants are not vaccinated before the age of 2 month in Germany (Empfehlung der Ständigen Impfkommission STICO, 2001) or 6 weeks in the USA (ACIP "Recommended Childhood Immunization Schedule, United States").

The delay in the development of the immune system is compensated in part by the transfer of maternal antibodies from the mother to the suckling during pregnancy or breast-feeding. However, not all infants are breastfed due to various reasons. Thus, there is a very critical period of time of about 6–8 weeks in humans during which the infant, having an immature and thus not fully functional immune system, does not receive maternal antibodies, and during which vaccination is usually not successful, or too dangerous.

The situation is very similar in mammalian animals, in particular for economically important animals such as cows, or companion animals, such as cats and dogs. To reduce costs, the amount of milk the calf receives from the mother is often drastically reduced. Instead, the calf receives a mixture of milk powder, starter and specific concentrated feed, sometimes already in the first week after birth. Consequently, the calf does not receive the necessary amount and variety of maternal antibodies, so the immature immune system is very susceptible to infections. Furthermore, farmers who breed calves and those who raise them for meat production are often not the same. At 4 to 6 weeks of age, calves from different breeder farms are pooled and shipped to other farms for meat production. At this time, when maternal antibodies are low and the immune system is not fully developed, the animals are exposed to new infectious agents under stressful conditions. This increases the risk for infections that could be prevented by vaccination. A similar situation can be found in cat or dog breeding facilities where the risk of infection is high.

OBJECT OF THE INVENTION

The object of the present invention is to provide a means to vaccinate newborn humans and animals, respectively, against foreign antigens and antigens that are associated with diseases in each group, respectively. More particularly, the object of the present invention is to provide a means for allowing the accelerated maturation of the immune system of newborn animals and humans. A further object of the present invention is to provide a means that allows vaccinating neonatal animals, including humans, against poxyirus infections, in particular against smallpox.

DETAILED DESCRIPTION OF THE INVENTION

According to the present invention, it was unexpectedly found that it is possible to safely and efficiently vaccinate, and/or treat, neonatal or prenatal animals, including humans, with viruses that are capable of infecting cells of the neonatal or prenatal animal, including a human, but not capable of being replicated to infectious progeny virus in said cells. In particular, it has been shown that the viruses used according to the present invention, such as MVA, in particular MVA-BN and its derivatives (see below), can be administered to newborns without showing any harmful effects. The vaccination of the animal with the virus leads to a specific immune response against the virus used for vaccination, and/or to a general vaccination against foreign antigens and tumor antigens, as explained below in detail. Moreover, the viruses used according to the present invention lead to an induction and/or enhancement of the maturation of the immune system, which is associated with an increase in the number of dendritic cells and factors such as interferons. Vaccination with the viruses used according to the present invention is possible even if the formulation administered to the animal does not include an adjuvant.

In summary, the viruses used according to the present invention (i) elicit an effective immune response in neonates, (ii) can be administered without the need of an adjuvant, and (iii) do not bear the risk of overwhelming the organism.

According to the present invention, the protective effect is exerted for at least 5 days, preferably for at least 7, 14, or 28 days after the first vaccination.

Viruses that are "capable of infecting cells" harbor structures on the viral surface that are capable of interacting with host cells to such an extent that the virus, or at least the viral genome, becomes incorporated into the host cell. Although, the viruses used according to the present invention are capable of infecting the host cell, they are not capable of being replicated to infectious progeny virus in the infected cells. In the context of the present invention, the term "virus not capable of being replicated to infectious progeny virus in said cells" refers to viruses with a genome that is at least partially transcribed and translated into viral proteins, or even replicated; however, not packaged into infectious viral particles. Thus, the viruses used according to the present invention, are viruses leading to abortive infections in the host. Abortive infections may occur for two reasons. According to the first alternative, a cell may be susceptible to infection but it may not permit multiplication of the virus; e.g., due to not having all the necessary viral genes for multiplication expressed and/or present in the viral genome. An example of this type of virus according to the present invention in human cells is Modified Vaccinia Virus Ankara (MVA), which is explained in more detail below. According to the second alternative, an abortive infection may also result from infection of cells with defective viruses, which lack a full complement of viral genes. An example of such a virus according to the present invention in human cells is DISC-HSV1 (disabled single-cycle Herpes simplex virus), i.e., a Herpes simplex virus, which is restricted to a single cycle of infection (Dilloo et al., Blood 1997, 89: 119–127). This virus lacks the gene for the essential glycoprotein H (gH), but can be grown to high titer in a complementing cell line expressing gH. In noncomplementing cell lines that are permissive for herpesvirus growth it is restricted to a single cycle of replication, leading to the release of noninfectious virus. The term "not capable of being replicated" refers preferably to viruses that do not replicate in the cells of the vaccinated animal. However, viruses showing minor residual replication activity that is controlled by the immature immune system of the neonate are within the scope of the present invention.

The virus, according to the present invention, may be any virus that is capable of infecting cells of the animal, but not capable of being replicated to infectious progeny virus in said cells. It is to be understood, that a virus capable of infecting cells of a first animal species, but not capable of being replicated to infectious progeny virus in said cells, may behave differently in a second animal species. In humans, for example, MVA-BN virus and its derivatives (see below) are capable of infecting human cells, but are not capable of being replicated to infectious progeny virus in said human cells. The same viruses, however, are very efficiently replicated in chickens, i.e., MVA-BN virus is capable of infecting chicken cells, and replicating to infectious progeny virus in chicken cells. One skilled in the art understands which virus to choose for a specific animal species. WO 02142480 discloses a test using murine strain AGR129, that allows determination of whether a virus is capable, or not, of being replicated in a neonatal or prenatal animal. The results obtained in this murine model are indicative for humans. Thus, the term "not capable of being replicated to infectious progeny virus" as used in the present application, corresponds to the term "failure to replicate in vivo" as used for mice in WO 02/42480. More details on this test are given below. The viruses according to the present invention are preferably capable of being replicated in at least one type of cell of at least one animal species. Thus, it is possible to amplify the virus prior to administration to the animal that is to be vaccinated and/or treated. By way of example, reference is made to MVA-BN that can be amplified in chicken embryonic fibroblast (CEF) cells, but is not capable of being replicated to infectious progeny virus in the neonatal or prenatal human. In this context, it is to be noted that chemically or physically inactivated viruses do not have all of the properties of this preferred embodiment. Inactivated viruses are capable of infecting cells of the neonatal or prenatal animal, including a human, and not capable of being replicated to infectious progeny virus in the neonatal or prenatal animal, including a human. However, inactivated viruses are not capable of replicating in at least one type of cell of at least one animal species. Preferably, the virus is a DNA virus. More preferably, for mammalian cells, in particular for human cells, the DNA virus is selected from DISC-Hepesviruses and Modified Vacciniavirus Ankara (MVA).

Modified Vaccinia Ankara (MVA) virus is related to Vaccinia virus, a member of the genera Orthopoxyirus in the family of Poxyiridae. MVA has been generated by 516 serial passages of the Ankara strain of vaccinia virus (CVA) (for review see Mayr, A., et al. Infection 3, 6–14 [1975]) in CEF. As a consequence of these long-term passages, the resulting MVA virus deleted about 31 kilobases of its genomic sequence and, therefore, was described as highly restricted to avian host cells (Meyer, H. et al., J. Gen. Virol. 72, 1031–1038 [1991]). It was shown, in a variety of animal models that the resulting MVA was significantly avirulent (Mayr, A. & Danner, K. [1978] Dev. Biol. Stand. 41: 225–34). Additionally, this MVA strain has been tested in clinical trials as a vaccine to immunize against the human smallpox disease (Mayr et al., Zbl. Bakt. Hyg. I, Abt. Org. B 167, 375–390 [1987], Stickl et al., Dtsch. med. Wschr. 99, 2386–2392 [1974]). These studies involved over 120,000 humans, including high risk patients, and proved that, compared to Vaccinia based vaccines, MVA had diminished virulence or infectiousness while it maintained good induction of immunity.

Preferred strains, according to the present invention, are MVA 575, deposited on Dec. 7, 2000, at the European Collection of Animal Cell Cultures (ECACC) with the deposition number V00120707; and MVA-BN, deposited on Aug. 30, 2000, at ECACC with the deposition number V000083008, and derivatives thereof, in particular if it is intended to vaccinate/treat humans. MVA-BN and its derivatives are most preferred for humans.

The properties of particularly preferred MVA strains, preferably the most preferred strains for humans, such as MVA-BN and its derivatives, can be summarized as follows:
(i) capability of reproductive replication in chicken embryo fibroblasts (CEF) and in baby hamster kidney cells (BHK), but no capability of reproductive replication in the human keratinocyte cell line, HaCat,
(ii) failure to replicate in vivo,
(iii) induction of a higher level of immunity compared to the known strain MVA 575 (ECACC V00120707) in a lethal challenge model and/or
(iv) induction of at least substantially the same level of immunity in vaccinia virus prime/vaccinia virus boost regimes when compared to DNA-prime/vaccinia virus boost regimes.

The preferred MVA strains according to the present invention possess property (ii) above, i.e., failure to replicate in the organism, which is to be vaccinated or treated and/or in the corresponding test system, as explained below. The preferred MVA strains preferably have two of the above properties. More preferably, the preferred MVA strains have three of the above properties. Most preferred are MVA strains having all of the above properties. An example of an MVA strain having all of the above properties in humans is MVA-BN. Preferred derivatives of MVA-BN are derivatives having in addition to feature (ii), at least one of the above properties, and more preferably at least two of the above properties. Most preferred are MVA-BN derivatives having all of the above properties.

Reference is made to WO 02/42480 for detailed information regarding assays used to determine whether a MVA strain has one, or more, of the above features (i) to (iv). The publication also discloses how viruses having the desired properties can be obtained. In particular, WO 02/42480 provides: a detailed definition of the features of MVA-BN and a derivative thereof; a detailed description of biological assays used to determine whether a MVA strain is MVA-BN or a derivative thereof; and methods to obtain MVA-BN or a derivative thereof. In other words, the features of MVA-BN; the description of biological assays allowing to evaluate whether a MVA strain is MVA-BN or a derivative thereof; and methods describing how to obtain MVA-BN, or a derivative thereof, are disclosed in WO 02/42480.

The procedures disclosed in WO 02/42480 are summarized below. This summary does not limit the relevance of this disclosure, the full extent of which is incorporated by reference.

The term "not capable of reproductive replication" in the cell line HaCAT (Boukamp et al. 1988, J Cell Biol 106(3): 761–71) is used in the present application as defined in WO 02/42480. Thus, a virus that is "not capable of reproductive replication" in the cell line HaCat, is a virus that shows an amplification ratio of less than 1 in the human cell line HaCat. Preferably, the amplification rate of the virus used as a vector according to the invention is 0.8, or less, in the human cell line HaCat. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells. The term "derivatives" of the viruses as deposited under ECACC V00083008 refers preferably to viruses showing essentially the same replication characteristics as the deposited strain, but showing differences in one, or more, parts of its genome. Viruses having the same "replication characteristics" as the deposited virus replicate with similar amplification ratios as the deposited strain in CEF cells and the cell lines BHK, HeLa, HaCat, and 143B. These viruses also show a similar replication in vivo, as determined in the AGR129 transgenic mouse model (see below).

The term "failure to replicate in vivo" is used in the present application as defined in WO 02/42480. Thus, the term refers to viruses that do not replicate in humans and in the murine model, as explained in WO 02/42480. The mice used in WO 02/42480 are incapable of producing mature B- and T-cells (AGR 129 mice). In particular, MVA-BN and its derivatives, do not kill AGR129 mice within a time period of at least 45 days, more preferably within at least 60 days, and most preferably within 90 days, after infection of the mice with $10^7$ pfu virus administered via intra peritoneum. Preferably, the viruses that show "failure to replicate in vivo" are further characterized in that no virus can be recovered from organs or tissues of the AGR129 mice 45 days, preferably 60 days, and most preferably 90 days after infection with 107 pfu virus administered via intra peritoneum. Instead of AGR129 mice, another mouse strain may be used which is incapable of producing mature B and T cells and, as such, is severely immune compromised and highly susceptible to a replicating virus.

The details of the lethal challenge experiment used to determine whether a MVA strain has "a higher immunogenicity compared to the known strain MVA 575" are explained in WO 02/42480. In such a lethal challenge model, unvaccinated mice die after infection with replication competent vaccinia strains such as the Western Reserve strain L929 TK+ or IHD-J. The infection with replication competent vaccinia viruses is referred to as "challenge" in the context of description of the lethal challenge model. Four days after the challenge, the mice are usually killed and the viral titer in the ovaries is determined by standard plaque assays using VERO cells. The viral titer is determined for unvaccinated mice and for mice vaccinated with MVA-BN and its derivatives. More specifically MVA-BN and its derivatives are characterized in that, in this test after vaccination with $10^2$ $TCID_{50}$/ml virus, ovarian virus titers are reduced by at least 70%, preferably by at least 80%, and more preferably by at least 90%, compared to unvaccinated mice.

In a preferred embodiment, the viruses according to the present invention, such as MVA, in particular MVA-BN and its derivatives, are useful for prime/boost administration. The viruses, in particular MVA strains that are most preferably used in the present invention, such as MVA-BN and its derivatives, as well as, corresponding recombinant viruses harboring heterologous sequences, can be used to efficiently first prime, and then boost immune responses in naive animals, as well as, in animals with a pre-existing immunity to poxyiruses. Thus, the most preferred virus according to the present invention induces at least substantially the same level of immunity in vaccinia virus prime/vaccinia virus boost regimes compared to DNA-prime/vaccinia virus boost regimes.

A vaccinia virus, in particular a MVA strain, is regarded as inducing at least substantially the same level of immunity in vaccinia virus prime/vaccinia virus boost regimes when compared to DNA-prime/vaccinia virus boost regimes, if the CTL response as measured in one of "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably the CTL response is higher in both assays.

The virus used according to the present invention, may be a non-recombinant virus, such as MVA, i.e., a virus that does not contain heterologous nucleotide sequences. An example of a non-recombinant vaccinia virus is MVA-BN and its derivatives. Alternatively, the virus may be a recombinant virus, such as a recombinant MVA containing additional additional nucleotide sequences that are heterologous to the virus.

The term "heterologous" as used in the present application, refers to any combination of nucleic acid sequences that are not normally found intimately associated with the virus in nature; such virus is also called a "recombinant virus".

The heterologous nucleic acid sequence is preferably selected from a sequence coding for at least one antigen, antigenic epitope, beneficial proteins, and/or therapeutic compound.

The term "beneficial proteins" as used in the present application refers to any proteins that are helpful in protecting an animal against an antigen selected from tumor antigen and foreign antigen, wherein the antigen is different from the antigens associated with the virus. Alternatively and more particularly, the "beneficial proteins" are active in (i) increasing the level of factors that activate dendritic cells; and/or (ii) increasing the number of dendritic cells; and/or (iii) increasing the production and/or cellular content of an interferon (IFN) or IL-12. Examples of such beneficial proteins are interferons such as IFN-alpha and IFN-beta, IL-12, Flt-3-L and GM-CSF.

The antigenic epitopes may be any epitope to which it makes sense to induce an immune response. Examples of antigenic epitopes are epitopes from Plasmodium falciparum, Mycobacteria, Influenza virus, viruses selected from the family of Flaviviruses, Paramyxoviruses, Hepatitis viruses, and Human immunodeficiency viruses, or viruses causing hemorrhagic fever such as Hantaviruses or Filoviruses, i.e., Ebola or Marburg virus. Thus, if e.g., a recombinant MVA expressing heterologous epitopes is used to vaccinate neonates according to the present invention, the result of this treatment is not only a general vaccination due to the accelerated maturation of the immune system, but also a specific vaccination against the heterologous epitope expressed from the heterologous MVA.

A "therapeutic compound" encoded by the heterologous nucleic acid in the recombinant virus can be, e.g., a therapeutic nucleic acid such as an antisense nucleic acid, or a peptide or protein with desired biological activity.

The insertion of a heterologous nucleic acid sequence is preferably into a non-essential region of the virus genome. Alternatively, the heterologous nucleic acid sequence is inserted at a naturally occurring deletion site of the viral genome (for MVA disclosed in PCT/EP96/02926). Methods of how to insert heterologous sequences into the viral genome, such as a poxyiral genome, are known to a person skilled in the art.

The present invention also provides a pharmaceutical composition and a vaccine comprising a virus according to the present invention, such as MVA, e.g., for inducing an immune response in a living animal body, including a human.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the virus or its recombinants are converted into a physiologically acceptable form. A person skilled in the art is familiar with such methods. For MVA and other poxyiruses, the vaccine can be prepared based on the experience in the preparation of poxyirus vaccines used for vaccination against smallpox (as described by Stickl, H. et al. [1974] Dtsch. med. Wschr. 99, 2386–2392). For example, the purified virus is stored at $-80°$ C. with a titre of $5\times10^8$ $TCID_{50}$/ml formulated in about 10 mM Tris, 140 mM NaCl pH 7.4. For the preparation of vaccine shots, e.g., $10^{1-108}$ particles of the virus, such as MVA, are lyophilized in 100 ml of phosphate-buffered saline (PBS) in the presence of 2% peptone and 1% human albumin in an ampoule; preferably a glass ampoule.

Alternatively, vaccine shots may be produced by stepwise, freeze-drying of the virus in a formulation. This formulation may contain additional additives such as mannitol, dextran, sugar, glycine, lactose or polyvinylpyrrolidone, or other additives such as antioxidants or inert gas, stabilizers or recombinant proteins (e.g. human serum albumin) suitable for in vivo administration. The glass ampoule is then sealed and can be stored between $4°$ C. and room temperature for several months. However, as long as no need exists, the ampoule is stored preferably at temperatures below $-20°$ C.

For vaccination or therapy, the lyophilisate can be dissolved in 0.1 to 0.5 ml of an aqueous solution, preferably physiological saline or Tris buffer, and administered either systemically or locally, i.e., by parenteral, intramuscular, or any other path of administration known to the skilled practitioner. The mode of administration, the dose, and the number of administrations, can be optimized by those skilled in the art in a known manner.

The virus according to the present invention, in particular MVA, can be administered by oral, nasal, intramuscular, intravenous, intraperitoneal, intradermal, intra-utero and/or subcutanous application. In small animals the inoculation for immunization is preferably given by parenteral, or nasal administration; whereas, in larger animals or humans, a subcutaneous, intramuscular, or oral inoculation is preferred.

MVA is administered preferably in a dose of $10^1$ $TCID_{50}$ (tissue culture infectious dose) to $10^9$ $TCID_{50}$.

As indicated above, the virus according to the present invention, in particular MVA, such as MVA-BN and its derivatives, may be administered in a therapeutically effective amount in a first inoculation ("priming inoculation") and in a second inoculation ("boosting inoculation").

In the context of the present invention the term "animal" also includes human beings. More generally, the animal is a vertebrate animal, preferably a mammalian animal, including a human. Specific examples of animals are pets, such as dogs, and cats; economically important animals such as calves, cattle, sheep, goats, horses, and pigs; and other animals such as mice and rats. MVA and DISC-HSV are particularly preferred viruses for these animal species, and humans. The invention may also be used for economically important birds such as turkeys, ducks, geese, and hens, if the viruses used are capable of infecting avian cells, but not capable of being replicated to infectious progeny virus in said cells.

The term "domestic animals" as used in the present description refers preferably to mammalian domestic animals; more preferably to dogs, cats, calves, cattle, sheep, goat, pigs, horses, and deer.

According to a first alternative, the viruses according to the present invention, in particular MVA-BN and its derivatives, may be used as specific vaccines, i.e., to elicit an immune response that protects the vaccinated newborn against diseases caused by a virulent virus belonging to the same virus group, family or genus as the virus that was used for vaccination. By way of example, MVA as defined above, in particular MVA-BN and its derivatives, can be used to vaccinate newborn humans against poxyirus infections, in particular against smallpox. MVA, in particular MVA-BN and its derivatives, may also be used to vaccinate vertebrate animals against poxyirus infections of veterinary importance. According to this first alternative, the virus used for vaccination may be a non-recombinant virus, such as MVA-BN or its derivatives, or a recombinant virus harboring genes in the viral genome that are not naturally found in said genome. Preferably, the recombinant virus harbors additional genes that are helpful in stimulating the immune response; e.g., cytokine genes and interferon genes.

According to a second, but related alternative, neonates are vaccinated with a recombinant virus harboring a heterologous nucleic acid sequence, as defined above, to induce an immune response against the amino acid sequence expressed from the heterologous nucleic acid sequence. By way of example, the nucleic acid sequence may code for an antigen or an antigenic epitope, as defined above. Examples of a recombinant virus according to this embodiment are recombinant MVA, in particular recombinant MVA-BN or a derivative thereof, comprising a heterologous nucleic acid coding for antigens from (i) viruses other than MVA, such as HIV-1, HIV-2, Denguevirus, West-Nile Virus, Japanese Encephalitis virus, measles virus, (ii) tumor antigens, (iii) bacteria, and (iv) fungi. If the antigen expressed from the recombinant virus is, e.g., a HIV antigen, it is possible to use the recombinant virus to induce an immune response in the vaccinated neonate against HIV and to prevent AIDS. In a broader sense, the recombinant virus expressing the antigen or antigenic epitope is used to induce an immune response against the agent from which the heterologous sequence is derived, and/or against the agent that comprises the antigen or antigenic epitope.

According to a third alternative, it has been unexpectedly found that viruses capable of infecting the cells of the neonatal or prenatal animal, including a human, but not capable of being replicated to infectious progeny virus in the neonatal or prenatal animal, including a human, can be used for the preparation of a medicament for protecting an animal, in particular a newborn animal, including a human, against an antigen selected from tumor antigens and foreign antigens, wherein the antigen is different from antigens associated with the virus.

According to this third alternative, newborns vaccinated with the viruses according to the present invention, in particular with MVA, such as MVA-BN and its derivatives, are protected against a challenge with foreign antigens such as infectious agents. Thus, the viruses according to the present invention, in particular MVA, are a general vaccine for newborns. That is, by vaccinating newborns with the viruses according to the present invention, in particular MVA, the immune system of the newborns becomes more competent to deal with foreign antigens such as viruses. In the Example section, this is exemplified for vaccination with MVA and a subsequent challenge with Herpes simplex virus type 1. Thus, if the virus according to the present invention, in particular MVA, is used for the vaccination of newborns, the vaccinated animals are more protected against foreign antigens than unvaccinated animals during the critical time span until a functional and mature immune system is established.

According to the present invention, "the tumor antigen and/or the foreign antigen is different from the antigens associated with virus". This term is to be interpreted, in that according to this embodiment, the invention is not primarily intended to use a virus, such as MVA, to induce an immune response against the virus itself.

Instead, the virus is used to induce an immune response, or at least a general immune stimulation, that protects the host against foreign antigens and tumor antigens that are not associated with the virus. The term "antigens associated with the virus" refers to epitopes and antigens of the virus particle, and to antigens and epitopes on the surface of a cell infected with the virus that are the result of the expression of the viral genome.

In the context of this embodiment, the term "foreign antigens" refers to antigens and epitopes that are not naturally a part, or a component, of the animal body. Foreign antigens are especially antigens and epitopes from infectious agents and toxins. Typical infectious agents are viruses such as herpesviruses, retroviruses, rabiesviruses, rhabdoviruses, and adenoviruses; bacteria such as Salmonella, Mycoplasm, Meningicoccus, Hemophilus; prions; or fungi.

The invention is not only of interest to vaccinate animals against foreign antigens but, in an alternative embodiment, is also suitable to vaccinate against tumor antigens. "Tumor antigens" are antigens associated with certain tumor-causing diseases. Tumor antigens are most often antigens encoded by the genome of the host that develops the tumor. Thus, in a strict sense, tumor antigens are not foreign antigens. However, tumor antigens are found in significant amounts in tumors; whereas, the amount of tumor antigens in normal tissue is significantly lower, and most often not found at all. Examples of tumor antigens are known to a person skilled in the art and include, e.g., MAGE antigens. MVA is effective against these tumor antigens since the vaccination of animals leads to an activation and/or accelerated maturation of the immune system that may then lead to the destruction of tumor cells.

The term "protecting against an antigen" refers to the development of an immune response, which is directed against the foreign or tumor antigen. If the foreign antigen is an infectious agent, the host is protected against the agent, i.e., the host develops an immune response against the antigen. Consequently, infection with the infectious agent leads to a less severe disease, or no disease at all. The term "protecting" is not to be understood in the sense that there is always a 100% protection against the foreign or tumor antigen. Instead, the term "protection" as used in the present application, refers to any beneficial effect that helps the animal deal with the foreign antigen and the tumor antigen, respectively.

According to the present invention such a protective effect is exerted for at least 5 days, preferably for at least 7, 14, or 28 days, after the first vaccination. In other words, the vaccinated and/or treated animal is protected, e.g., against a foreign antigen if the animal comes into contact with the antigen after 5, 7, 14, and 28 days, respectively.

In the context of the present invention, the effect of the vaccination of newborns with the virus according to the present invention, in particular with MVA, may be explained by the induction or enhancement of maturation of the immune system, and/or the activation of the immune system. In the context of the present invention, the term "induction or enhancement of the maturation of the immune system" refers inter alia to the accelerated increase of dendritic cells or their precursors in vaccines, relative to controls. The terms "acceleration of the maturation" of the immune system and "enhancement of the maturation" of the immune system are used interchangeably in this description.

The "activation of the immune system" is characterized by the secretion and/or cell surface expression of molecules and hormones that facilitate cell/cell interaction or trafficking. Specific receptors take up these signals and respond accordingly. Activation markers are inter alia Flt3-L, IL-12, IFN-alpha, MHC-II and CD8, in particular CD8alpha (see below).

The accelerated development/maturation of the immune system is correlated with (i) an increase in the level of factors activating and or mobilizing dendritic cells (DC) or their precursor cells; and/or (ii) an increase in the number of dendritic cells and their precursor cells; and/or (iii) an increase in the production and/or cellular content of an interferon or IL-12. An example of DC precursor cells that are induced by a virus according to the present invention, in particular by MVA, are plasmocytoid DC precursors which are very important in defense against viral infections, and which seemingly produce IFN $\alpha/\beta$.

More specifically, the enhancement of the maturation of the immune system is preferably defined by at least a 2-fold increase in surface markers found on DC, such as MHC-II, CD40 and/or CD80/86. Preferably, such an increase can be measured in the blood. Additional markers that characterize enhancement of the maturation of the immune system are Flt3-L, IL-12, IFN-alpha, MHC-II and CD8a (see below). Moreover, accelerated maturation of the immune system is preferably correlated to at least a 1.5 fold increase, preferably at least a 2.0 fold increase, in the number of CD11c positive cells in the blood, and/or the spleen, 7 days after the administration of MVA-BN to newborn animals, when compared to control animals that have not received MVA-BN. Moreover, the enhancement of maturation of the immune system may preferably be correlated with at least a 1.5 fold increase, more preferably at least a 2.0 fold increase, in the concentration of Flt3-L two days after the vaccination of neonates with viruses according to the present invention, when compared to age matched controls.

In this context, it is to be noted that there is an association between the phenotype and function of murine and human DC populations that can be characterized by their surface phenotype (Hochrein et al. 2002. *Hum. Immunol.* 63: 1103). Dendritic cells in the blood can be detected by flow cytometry using a range of surface markers (MacDonald et al. 2002. *Blood.* 100:4512) that allow specific populations of DC, such as plasmaytoid DC, to be identified (Dzionek et al. 2002. *Hum Immunol.* 63: 1133; Dzionek et al 2000. *J. Immunol.* 165: 6037). Using similar techniques, DC can also be detected in other human tissues (Summers et al. 2001. *Am. J. Pathol.* 159: 285).

According to the present invention, the viruses as defined above might also be used to treat neonatal or prenatal animals to (i) increase the level of factors activating and/or mobilizing dendritic cells (DC) or their precursor cells; and/or (ii) to increase the number of dendritic cells and their precursor cells; and/or (iii) to increase the production and/or cellular content of an interferon or IL-12. It has been demonstrated that following vaccination with MVA-BN, the plasmocytoid dendritic cells upregulate MHC-II and CD8a, and produce significantly more IL-12 and IFN-alpha. The increase of IL-12 after the administration of the viruses used according to the present invention is preferably 2-fold, more preferably 100-fold, 500-fold, 1000-fold, 2500-fold or 5000-fold. The increase of the concentration of Flt3-L two days after the vaccination of neonates with viruses according to the present invention, most preferably with MVA-BN or its derivatives, is preferably 1.5-fold, more preferably 2.0-fold, when compared to age matched controls.

The term "activation of dendritic cells or their precursors" refers to the maturation of DC to antigen presenting cells through ill-defined cell stages driven by hormones and different antigenic stimuli. Intermediates of DC are termed precursors. These immature DC reach the periphery. Activation markers that are upregulated in activated dendritic cells are inter alia Flt3-L, IL-12, IFN-alpha, MHC-11 and CD8a (see below).

It was noted that hormones such GM-CSF, lead to more immature DC in the periphery. Because GM-CSF leads to more DC precursor in bone marrow, blood and peripheral organs (and the cells have to move there), this phenomenon has been termed "mobilization of dendritic cells or their precursors". This definition is also used in the present description.

Consequently, the vaccination of animals, including a human, is especially useful if it is intended to (i) increase the level of factors activating dendritic cells (DC) or their precursor cells; and/or (ii) increase the number of dendritic cells or their precursor cells; and/or (iii) increase the production and/or cellular content of an interferon or IL-12.

Factors that activate dendritic cells include inter alia Flt3-L (Lyman et al., Cell 1993, 75: 1157–1167) and GM-CSF. Typical interferons according to the present invention are IFN-alpha and IFN-beta. The viruses used according to the present invention induce Flt3-L and it is assumed that some of the beneficial effects observed are due to said induction.

In the context of the present application, a newborn animal, or human, is defined as an animal or human, not yet having a mature immune system. Throughout this specification, the terms "newborn animal" and "neonatal animal" are used synonymously. A mature immune system is characterized by the ability to fully activate the innate immune system, and by the fact that all known T and B cell functions and products are in place; in particular immunoglobulin isotypes such as IgA and IgE. Thus, an immature immune system is characterized by a low number of T cells, B cells, and dendritic cells, relative to adults; by low IFN production compared to adults; and by secondary lymphoid organs that are not fully mature. More specifically, a "neonatal" or "newborn" in the context of the present invention may be defined as an infant animal having a number of splenic CD4+ cells being preferably at least 2-fold, more preferably at least 20-fold, more preferably at least 200-fold, more preferably at least 2,000-fold, and most preferably at least 20,000-fold lower than the average number of splenic CD4+ cells in adults.

In mice, the immune system is mature at the age of 4 weeks. In humans, maturity is probably achieved at 6 month to 1 year of age. In cats and dogs, the immune system is mature usually at the age of 6 month; and in calves, sheep and pigs at the age of 4–12 weeks. Vaccination with the virus according to the present invention, in particular with MVA, is preferably done before the immune system is mature. However, since maturity develops almost exponentially after birth, it is most preferred to vaccinate with the virus according to the present invention, in particular with MVA, as early after birth as possible. Since in all relevant domestic animals, and in humans, the immune system is mature no earlier than 4 weeks after birth, it is generally preferable that vaccination with the virus according to the present invention, in particular with MVA, is done within 4 weeks after birth, more preferably within 2 weeks after birth, even more preferably within 1 week after birth, and most preferably within 3 days after birth. These general terms are applicable to all important domestic animals, in particular to important domestic mammalian animals, and humans. A person skilled in the art will be aware of the fact that even older animals may be regarded as newborns/neonatals in the context of the present invention; and therefore, vaccination may also be successfully carried out with older animals, when the immune system is not yet mature 4 weeks after birth. Thus, in humans, the vaccination may be carried out within 6 month after birth, more preferably within 3 month after birth, more preferably within 2 month after birth, more preferably within 4 weeks after birth, more preferably within 2 weeks after birth, even more preferably within 1 week after birth, and most preferably within 3 days after birth.

Since the best effects of the virus according to the present invention, in particular MVA, as a general vaccine are observed if the virus is administered to an immature immune system, it may be preferred to vaccinate even prenatal animals, including humans. Prenatal vaccination may be desirable in economically important animals such as cattle or pigs. If the placenta allows passage of the virus, the prenadte can be vaccinated simply by vaccinating the mother animal. Thus, the vaccination of the mother animal to vaccinate the prenate is particularly promising in an animal having a placenta endotheliochorialis, such as dogs, cats, rats, and mice; or animals having a placenta heamochorialis, such as primates, including humans. In animals having a placenta chorionepithelialis, such as cattle and sheep, or animals having a placenta syndesmochorialis, such as pigs and horses, the vaccination of prenates can be preferably done by in-utero administration. Of course, this mode of administration can be also done for animal having a placenta endotheliochorialis or haemochorialis.

Since the viruses according to the present invention, in particular MVA, lead to an accelerated maturation of the immune system and are thus, useful as a general vaccine, the vaccinated animals are protected against a variety of diseases. More specifically, the viruses according to the present invention, in particular MVA, can be used to vaccinate cats for general well being and against feline herpes or feline infectious peritonitis. The viruses according to the present invention, in particular MVA, may be used in dogs for general well being and against respiratory tract associated (viral) diseases. The viruses according to the present invention, in particular MVA, may be used in pigs for general well being and against Hemophilus or Mycoplasm infections; and especially in fattening pigs.

As previously indicated, it is a preferred embodiment to use the viruses according to the present invention, in particular MVA, in newborns or prenatal animals to protect the animal against a foreign antigen and/or a tumor antigen, wherein the tumor antigen is different from the antigens associated with the virus used for vaccination. However this embodiment is not restricted to newborn and prenatal animals. Instead, in an alternative embodiment, the invention can be carried out for animals of all ages, since a beneficial effect can be observed also in adult animals. Thus, according to this embodiment, the viruses as defined above, in particular MVA-BN and its derivatives, are useful to protect an animal, including a human, against an antigen selected from tumor antigens and foreign antigens, wherein the antigen is different from the antigens associated with the virus. As indicated above, the viruses used according to the present invention are capable of infecting cells of the animal, but not capable of being replicated to infectious progeny virus in said cells. All information, definitions, including the definition of the duration of the protective effect, examples, as well, as the preferred, more preferred and most preferred embodiments given above for neonates, also apply for the present embodiment according to which the virus may also be administered to adults.

In contrast to newborns, the immune system of adult animals has already matured. Nevertheless, it may be that the immune system is weakened due to certain diseases, or simply due to the age of the animal. Especially in immune-compromised or elderly individuals, the administration of the viruses according to the present invention, in particular MVA, may have a beneficial effect inter alia by (i) increasing the level of factors activating and/or mobilizing dendritic cells (DC) or their precursor cells; and/or (ii) by increasing the number of dendritic cells or their precursor cells; and/or (iii) by increasing the production and/or cellular content of an interferon or IL-12. Thus, even in adult animals, the administration of the viruses according to the present invention, in particular MVA, may lead to an increased competence of the immune system to deal with foreign and/or tumor antigens. In other words, the viruses used according to the present invention are useful for the activation of the immune system, in general.

The invention further concerns viruses according to the present invention, in particular MVA, for the preparation of a medicament to be administered to an animal, including a human, wherein said medicament (i) increases the level of factors which activate dendritic cells; and/or (ii) increases the number of dendritic cells; and/or (iii) increases the production and/or cellular content of an interferon (IFN) or IL-12. All definitions provided above for the other embodiments are also applicable for the present embodiment. According to this embodiment, the invention does not aim primarily at inducing a protection against foreign antigens and/or tumor antigens. Instead, this embodiment is aimed at treating conditions and diseases characterized by (i) a low level of factors which activate dendritic cells; and/or (ii) insufficient or too low number of dendritic cells; and/or (iii) low production and/or cellular content of an interferon (IFN) or IL-12. Thus, according to this embodiment the treatment with viruses according to the present invention, in particular MVA, could protect against allergies or autoimmune diseases. Again, this treatment is particularly promising if the viruses according to the present invention, in particular MVA, are administered to newborn animals.

Additionally, according to a further embodiment, the virus according to the present invention, such as MVA, in particular MVA-BN and its derivatives, is particularly useful to induce immune responses in immuno-compromised animals, e.g., monkeys (CD4<400 µl of blood) infected with SIV, or in immuno-compromised humans. The term "immuno-compromised" describes the status of the immune system of an individual, which shows only incomplete immune responses or has a reduced efficiency in the defense against infectious agents.

The invention further concerns a method for protecting an animal, including a human, against an antigen selected from tumor antigen and foreign antigen, by administration of a virus according to the present invention, in particular Modified Vaccinia virus Ankara (MVA), wherein the tumor antigen and/or the foreign antigen is different from the antigens associated with the virus.

In a further embodiment the invention concerns a method for the treatment of an animal, including a human, comprising the administration of a Modified Vaccinia virus Ankara (MVA) to (i) increase the level of factors which activate dendritic cells; and/or (ii) increase the number of dendritic cells; and/or (iii) increase the production and/or cellular content of an interferon (IFN) or IL-12.

SUMMARY OF THE INVENTION

A use of a virus for the preparation of a medicament for the vaccination or treatment of a neonatal or prenatal animal, including a human, wherein the virus is capable of infecting the cells of the neonatal or prenatal animal, including a human, but not capable of being replicated to infectious progeny virus in the neonatal or prenatal animal, including a human.

A method for the treatment or vaccination of a neonatal or prenatal animal, including a human, comprising the administration of a virus, wherein the virus is capable of infecting the cells of the neonatal or prenatal animal, including a human, but not capable of being replicated to infectious progeny virus in the neonatal or prenatal animal, including a human.

A virus for the vaccination or treatment of a neonatal or prenatal animal, including a human, wherein the virus is capable of infecting the cells of the neonatal or prenatal animal, including a human, but not capable of being replicated to infectious progeny virus in the neonatal or prenatal animal, including a human.

A use, method or virus as defined above, wherein the virus is a DNA virus.

A use, method or virus as defined above, wherein the virus is selected from DISC-Herpesviruses and Modified Vaccinia Virus Ankara (MVA).

A use, method or virus as defined above, wherein the MVA strain is MVA-BN, deposited at the European Collection of Animal Cell Cultures (ECACC) with the deposition number V00083008, and derivatives thereof.

A use, method or virus as defined above, wherein MVA is administered by oral, nasal, intramuscular, intravenous, intraperitoneal, intradermal, intra-utero and/or subcutanous application.

A use, method or virus as defined above, wherein MVA is administered in a therapeutically effective amount in a first inoculation ("priming inoculation") and in a second inoculation ("boosting inoculation").

A use, method or virus as defined above, wherein MVA is administered to the animal, including a human, in an amount of at least $10^1$ TCID$_{50}$ (tissue culture infectious dose).

A use, method or virus as defined above, wherein the vaccination is against a poxyirus infection.

A use, method or virus as defined above, wherein the poxyirus infection is a smallpox infection.

A use, method or virus as defined above, wherein the virus genome comprises at least one heterologous nucleic acid sequence.

A use, method or virus as defined above, wherein the heterologous nucleic acid sequence is selected from a sequence coding for at least one antigen, antigenic epitope, and/or a therapeutic compound.

A use, method or virus as defined above, wherein the vaccination is against the agent from which the heterologous sequence is derived or the agent that comprises at least one antigen or antigenic epitope.

A use, method or virus as defined above, wherein the vaccination is for protecting the animal, including a human, against an antigen selected from tumor antigen and foreign antigen, wherein the tumor antigen and/or the foreign antigen is different from the antigens associated with the virus.

A use, method or virus as defined above, wherein the foreign antigen is selected from infectious agents and toxins.

A use, method or virus as defined above, wherein the infectious agent is selected from viruses, bacteria, prions and fungi.

A use, method or virus as defined above, wherein the vaccination or treatment is used to induce or enhance the maturation and/or activation of the immune system.

A use, method or virus as defined above, wherein the treatment is used to (i) increase the level of factors which activate and/or mobilize dendritic cells or their precursor cells, (ii) increase the number of dendritic cells or their precursor cells or (iii) increase the production and/or cellular content of an interferon (IFN) or IL-12.

A use, method or virus as defined above, wherein the factor which activates the dendritic cells is Flt3-L and/or GM-CSF.

A use, method or virus as defined above, wherein the interferon is IFNα and/or IFNβ.

A pharmaceutical composition comprising a virus as defined above.

A vaccine comprising a virus as defined above.

A virus for administration to a neonatal or prenatal animal, including a human, wherein the virus is capable of infecting the cells of the neonatal or prenatal animal, including a human, but not capable of being replicated to infectious progeny in the neonatal or prenatal animal, including a human.

A virus as defined above, which is a DNA virus.

A virus as defined above, which is DISC-Herpesvirus or Modified Vaccinia Virus Ankara (MVA).

A virus as defined above, wherein the MVA strain is MVA-BN, deposited at the European Collection of Animal Cell Cultures (ECACC) with the deposition number V00083008, and derivatives thereof.

A virus as defined above, wherein the virus genome comprises at least one heterologous nucleic acid sequence.

A virus as defined above, wherein the heterologous nucleic acid sequence codes for antigens selected from bacteria, fungi, tumor cells, and viruses other than that used for administration.

A virus as defined above, wherein the heterologous nucleic acid sequence is selected from a sequence encoding for at least one antigen, antigenic epitope, and/or a therapeutic compound.

A virus as defined above, which induces an immune response against the amino acid sequence expressed from the heterologous nucleic acid.

A virus as defined above, wherein the heterologous nucleic acid encodes a foreign antigen or a tumor antigen.

A virus as defined above, which protects the neonatal or prenatal animal, including a human, against a tumor antigen or foreign antigen, wherein the tumor antigen and/or the foreign antigen is different from antigens associated with the virus.

A virus as defined above, wherein the foreign antigen is a toxin, or an infectious agent selected from viruses, bacteria, prions and fungi.

A virus as defined above, which protects the neonatal or prenatal animal, including a human, against infections with virulent viruses belonging to the same virus group, family, or genus, as the virus used for vaccination.

A virus as defined above, which is a Modified Vaccinia Virus Ankara and which protects a human against smallpox.

A method of vaccinating, treating, or protecting a neonatal or prenatal animal, including a human, against an antigen or an agent comprising said antigen, comprising the step of administering an effective amount of a virus as defined above, to the neonatal or prenatal animal, including a human, for the vaccination, treatment, or protection, thereof.

A method as defined above, wherein the antigen is selected from (i) antigens from pathogenic viruses belonging to the same virus group as the virus used for administration, (ii) antigens from a heterologous gene product expressed by the virus used for administration, and (iii) antigens from a foreign or tumor antigen that is not associated with the virus used for administration.

The method as defined above, wherein the virus is administered by oral, nasal, intramuscular, intravenous, intraperitoneal, intradermal, intra-utero and/or subcutaneous application.

The method as defined above, wherein the virus is administered in a therapeutically effective amount in a first or priming inoculation, and in a second or boosting inoculation.

The method as defined above, wherein the virus is administered in an amount of at least $10^1$ TCID$_{50}$ (tissue culture infectious dose).

The method as defined above, wherein the vaccination is against a poxyirus infection.

The method as defined above, wherein the poxyirus infection is a smallpox infection.

The method as defined above, wherein the vaccination is against an agent from which the heterologous sequence inserted into the virus, or the antigen or antigenic epitope expressed from the virus, is derived.

The method as defined above, wherein the foreign antigen is selected from infectious agents and toxins.

The method as defined above, wherein the infectious agent is selected from viruses, bacteria, prions and fungi.

The method as defined above, wherein the virus is MVA-BN, deposited at the European Collection of Animal Cell Cultures (ECACC) with the deposition number V00083008, and derivatives thereof.

The method as defined above, wherein the vaccination is against a poxyirus infection.

The method as defined above, wherein the poxyirus infection is a smallpox infection.

A method of vaccinating, treating, or protecting a neonatal or prenatal animal, including a human, with a virus as above to (i) increase the level of factors which activate and/or mobilize dendritic cells or their precursor cells, (ii) increase the number of dendritic cells or their precursor cells or (iii) increase the production and/or cellular content of an interferon (IFN) or IL-12.

The method as defined above, wherein the dendritic cells are activated by Flt3-L and/or GM-CSF.

The method as defined above, wherein the interferon is IFNα and or IFNβ.

The method as defined above, wherein the virus is MVA-BN, deposited at the European Collection of Animal Cell Cultures (ECACC) with the deposition number V00083008, and derivatives thereof.

A method of inducing or enhancing the maturation and/or activation of the immune system of a neonatal or prenatal animal, including a human, comprising the step of administering an effective amount of a virus as defined above, to the neonatal or prenatal animal, including a human, for inducing the maturation and/or activation thereof.

The method as defined above, wherein the virus is administered by oral, nasal, intramuscular, intravenous, intraperitoneal, intradermal, intra-utero and/or subcutaneous application.

The method as defined above, wherein the virus is administered in a therapeutically effective amount in a first or priming inoculation, and in a second or boosting inoculation.

The method as defined above, wherein the virus is administered in an amount of at least $10^1$ TCID$_{50}$ (tissue culture infectious dose).

The method as defined above, wherein the virus is MVA-BN, deposited at the European Collection of Animal Cell Cultures (ECACC) with the deposition number V00083008, and derivatives thereof.

A pharmaceutical composition, comprising as active principle a virus as defined above, together with one or more pharmaceutically acceptable excipients or vehicles.

SHORT DESCRIPTION OF THE FIGURES

FIG. 1A: Newborn mice were injected once within 24–48 h of birth with $10^6$ p.f.u. of MVA or DISC HSV-1 or treated with physiological saline (NaCl) as controls. At 7 days of age, CD11 c, a pan DC marker, was used to determine these cells in peripheral blood by flow cytometry. Mean and standard deviation of 3 to 5 experiments are shown.

Figure 1B:
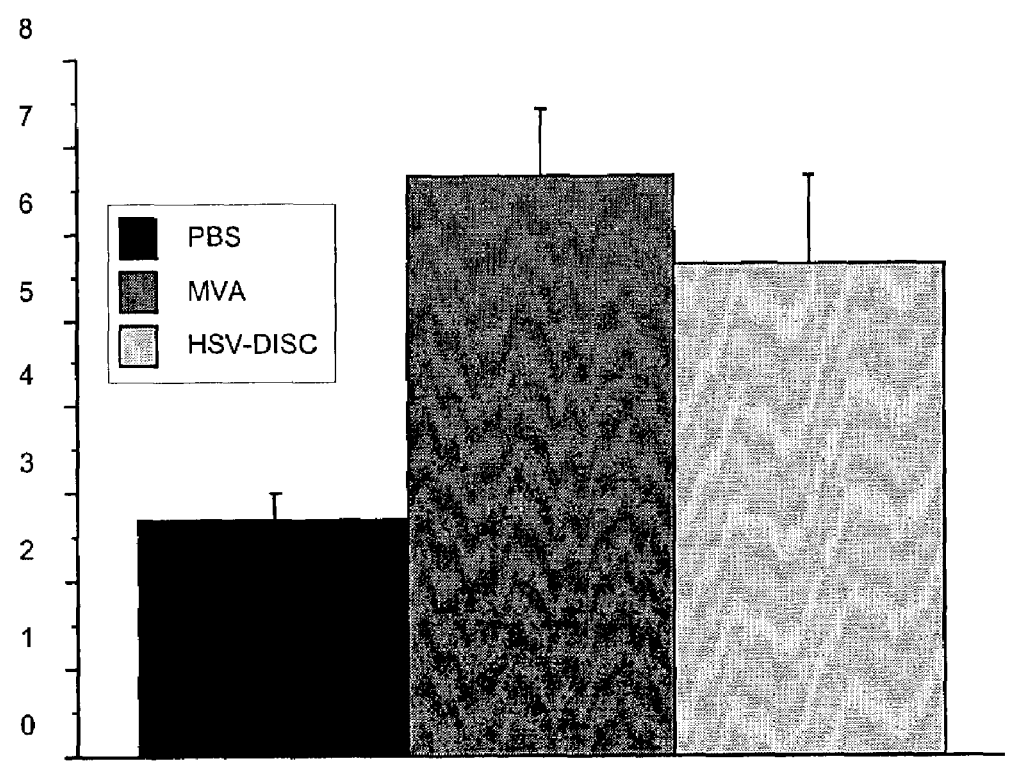

FIG. 1B: Experiment as in FIG. 1A. However, CD11c cells were determined in spleen by flow cytometry FIG. 1C: Experiment as in FIG. 1A. However, CD11c cells were determined in peritoneal fluid by flow cytometry FIG. 2: Mice were vaccinated with MVA-BN as indicated in the left column. After two weeks the percentage of CD11c$^+$ single and CD11c$^+$/CD8+ double positive cells in spleen and in blood were determined by flow cytometry.

Figure 3:
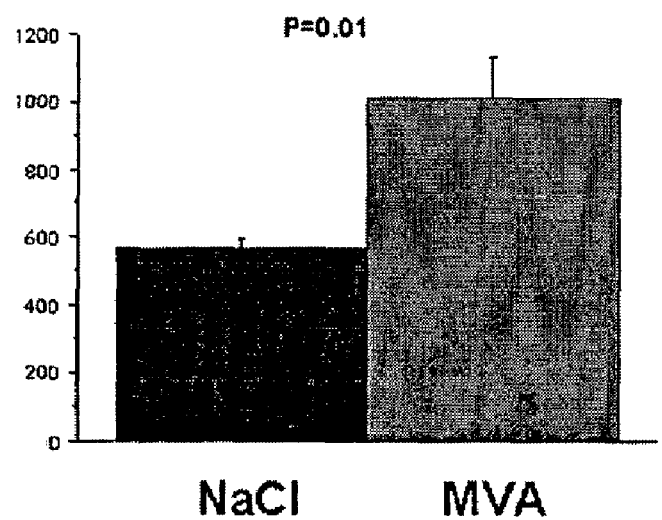

FIG. 3: Newborn mice were injected with MVA, or NaCl as control, at day one and 5 of age. At day 8, murine Flt3-L was determined in serum of these mice by ELISA and the values are given as pg/ml FIG. 4: Newborn mice were injected once within 24–48 h of birth with $10^6$ p.f.u. of MVA or treated with NaCl as controls. At 7 days of age, all mice were exposed to 100×LD$_{50}$ of HSV-1 strain F. The number of surviving animals was monitored for 21 days.

FIG. 5: Mice were treated as in FIG. 4. The data represent 9 different challenge experiments with 100 LD$_{50}$ of HSV-1. None of the control animals survived the challenge.

Figure 6:
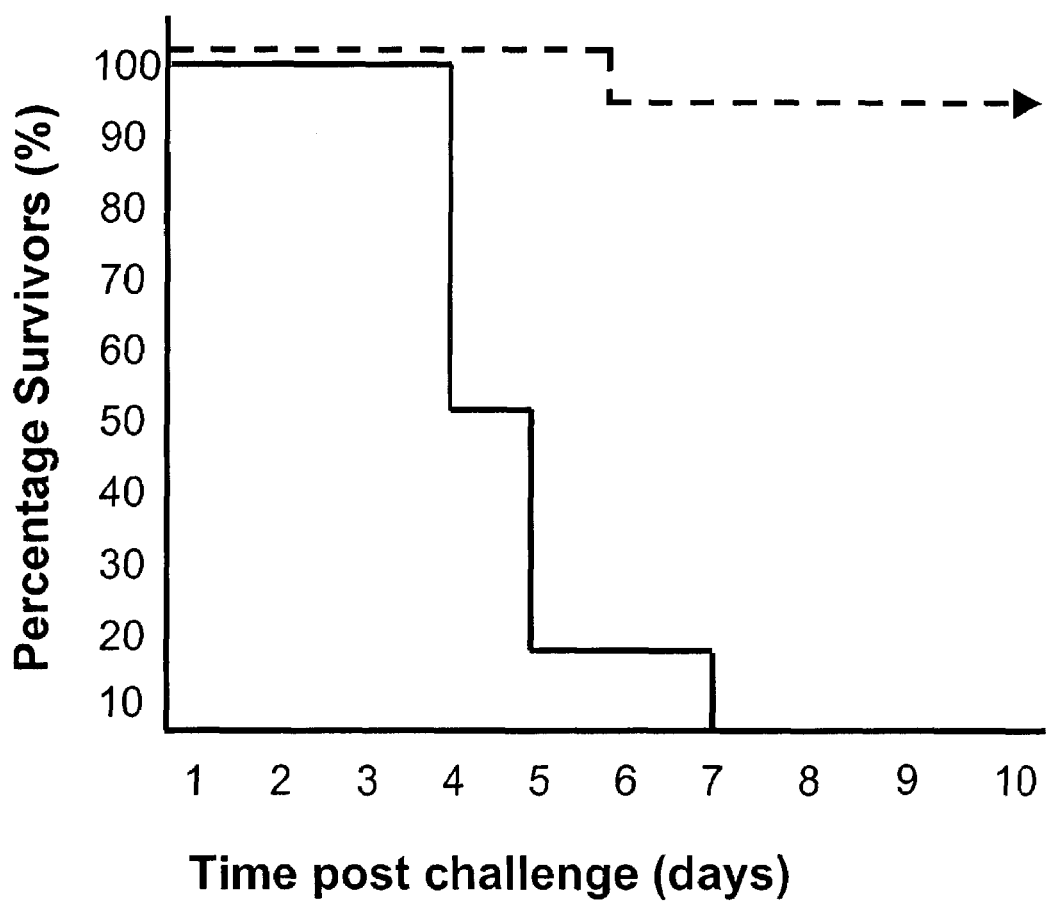

FIG. 6: Survival of adult mice vaccinated on the first day of life with MVA-BN following a lethal vaccinia challenge. Three litters of six 1-day-old pups (18 mice) were vaccinated with MVA-BN (2.5×10$^7$ TCID$_{50}$) and at 4 weeks (adult mice) challenged with a lethal dose of vaccinia. MVA-BN vaccination clearly induced a protective immunity in neonatal mice that lasted until adulthood.

EXAMPLES

The following examples further illustrate the present invention. It should be well understood by a person skilled in the art, that the provided examples may not be interpreted in any way that limits the applicability of the technology provided by the present invention to these Examples.

Example 1

(i) MVA-BN and DISC-HSV Induce DC of the CD11c$^+$ and CD8$^+$ Phenotype in Newborn Animals First set of experiments: Newborn mice are naturally immunodeficient because the IFN system is not mature. The number and activation state of DC, the best producers of IFN known today, has not been analyzed. DC can be induced in vitro, as well as, in vivo by a variety of stimuli. These studies tested whether a controlled MVA-BN replication could induce DC, and also analyzed their phenotype. Groups of mice were injected with $10^6$ plaque forming units (p.f.u.) of MVA-BN, or saline only, within 1–2 days after birth, and in some cases, 5 days after birth. Blood and spleen cells from individual mice of both groups were analyzed by FACS and the data compared.

Data from 7 to 8 individual mice indicated that treatment with MVA-BN increased CD11c$^+$ cells by 2 to 3-fold, accompanied by an increased expression of MHC II and increased presence of T cells of the CD4 or CD8 type. Interestingly, CD19/54, a marker for mature B cells, decreased; thereby, indicating that either (i) these cells emigrated in organs other than the spleen, or (ii) that precursor of B cells were recruited early to other lineages, notably DC of the plasmocytoid phenotype that carry early B cell markers (B220).

Data from three different experiments indicated reproducibility and significant differences. Experiments with DISC-HSV-1, a different replication controlled viral vaccine, induced similar amounts of CD11c+ cells after neonatal priming.

Figure 1C:
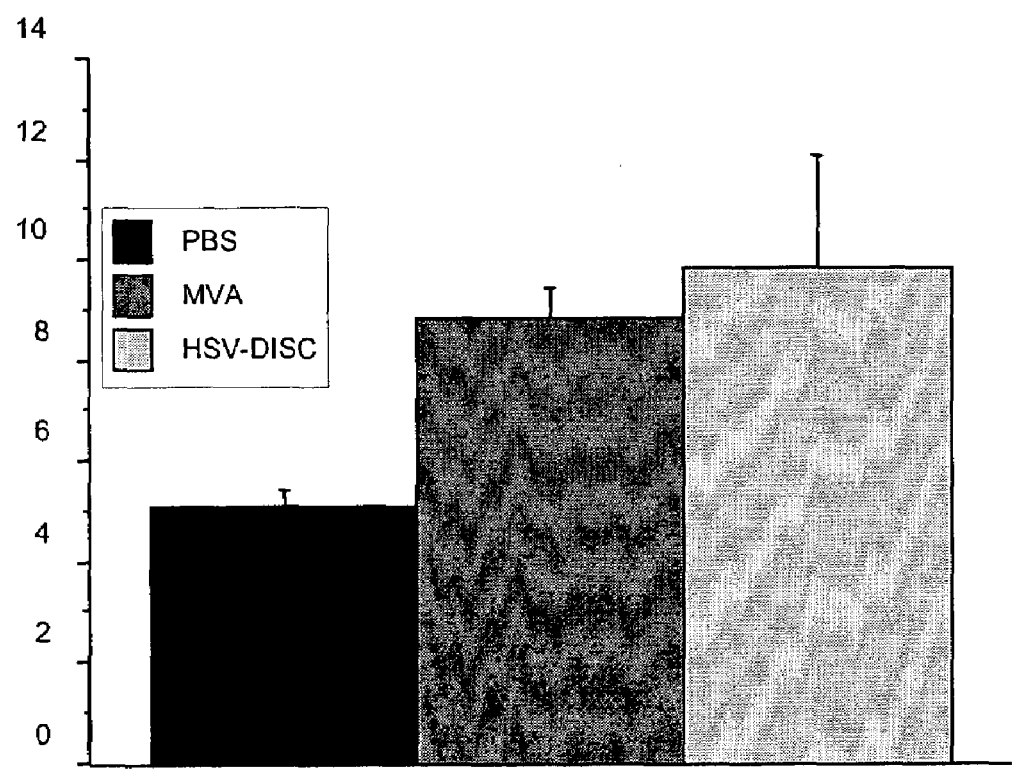

The results are summarized in FIGS. 1A–C.

To further investigate subpopulations of DC in blood and spleen, and analyze long-term effect of treatment with MVA-BN, cells in blood and spleen were analyzed at 2 weeks of age. At this time point, treated animals had about twice the number of CD11c$^+$ cells in the spleen than at one week of age. However, a single treatment with the virus at birth led to a 3-fold increase in the number of these cells in the spleen 2 weeks later (FIG. 2). Similar effects were seen in blood, with the exception that CD11c+/CD8a+ were about 4 times higher. A single treatment with MVA-BN at 7 days of birth led to an increase of CD11c+/CD8a+ from 13 to 40-fold, with a less dramatic effect on the CD11c$^+$ cells. As expected, two vaccinations, at birth and day 7, had a significant effect on CD11c$^+$ cells. The various effects are shown in FIG. 2.

Second set of experiments: One-week-old mice that were vaccinated at birth with 2.5×10$^7$ TCID$_{50}$ of MVA-BN showed a different composition of immunologically relevant cell populations in spleen and in blood than control mice (Table 1). In blood, there was an increase in the CD8 positive lymphocyte population, as well as, an increase in the number of NK cells. The number of CD11c positive cells was about 3-fold higher than in controls, and the percent of B-cells (B220 and CD19 double positive cells) was significantly decreased. In the spleen, the total number of cells did not differ between immunized animals and controls. In contrast to the blood, the spleen of vaccinated animals had more CD4 positive T lymphocytes than controls, and the number of NK cells was not increased. Similar to blood, the relative number of CD8 positive lymphocytes was increased and the number of B-cells decreased. The percentage of CD11c positive cells was about 3-fold higher than in controls. A difference in the percentage of dendritic cells was recognized at day 5 following vaccination with MVA-BN, when the number of CD11c positive cells in the spleen of 4 untreated controls was 3.6%, compared to 4.8% in four MVA-BN vaccinated mice. The same amount of UV-inactivated MVA-BN did not cause any significant change in the cell populations after vaccination of neonatal mice, compared to controls (data not shown). The initial vaccination dose was chosen arbitrarily. After titration of the inoculum, a standard dose of $2.5 \times 10^6$ TCID$_{50}$ was selected for vaccination (10 time less than in the initial experiment). At this dose, maximal numbers of DC were induced (Table 2).

significantly higher in MVA-BN treated mice (5.6±0.7%) than in both control groups (untreated 3.0±0.3%, p=0.01; UV-inactivated MVA-BN 3.0±0.2%, p=0.006. Mann-Whitney U-test).

(iii) Neonatal Mice Treated With MVA-BN Have Elevated Levels of serum Flt3-L

Flt3-L is a hematopoetic factor that leads to increased levels of DC in adult animals. In humans and possibly mice, the richest source of this factor is activated T cells. To determine whether the elevated numbers of DC could be the result of induced Flt3-L, serum of MVA-BN treated mice was compared to mock treated animals for the presence of this factor. Animals treated at day 2 and 5 had twice the levels of Flt3-L in the serum when compared to serum of mock treated animals. Hence, Flt3-L is one of the factors that could be made responsible for elevated numbers of DC (FIG. 3)

The time course of the Flt3-L induction in newborn mice was assessed after administration of MVA-BN. In newborns, MVA-BN vaccination induced an increase in Flt3-L concentration within 24 hours. The induction reached a maximum after 48 hours and was still present at day 7, the time when spleen cells were usually analyzed and resistance against HSV-1 was tested (see below). In the vaccinated mice, the Flt3-L concentration in the serum was increased 2-fold 24 hours and 48 hours after the vaccination, compared with age matched control animals.

TABLE 1

Changes induced in blood and spleen cells in newborn mice 1 week after immunization with $2.5 \times 10^7$ TCID$_{50}$ MVA-BN

| Parameter % | Blood | | | Spleen | | |
|---|---|---|---|---|---|---|
| | NaCl | MVA-BN | P* | NaCl | MVA-BN | P* |
| Total cells ×10$^6$ | | | | 17.9 ± 1.9 | 24.1 ± 2.6 | 0.105 |
| % CD11c | 5.4 ± 1.3 | 18.6 ± 1.5 | 0.001 | 2.8 ± 0.1 | 7.9 ± 0.8 | 0.001 |
| % CD11c/CD8α | 0.5 ± 0.1 | 2.7 ± 0.3 | 0.001 | 1.1 ± 0.1 | 4.6 ± 0.7 | 0.002 |
| % CD4/CD3 | 16.9 ± 1.1 | 16.1 ± 1.5 | 0.999 | 94.8 ± 0.3 | 8.1 ± 1.5 | 0.004 |
| % CD8α/CD3 | 6.0 ± 0.9 | 10.3 ± 0.9 | 0.002 | 4.7 ± 0.3 | 8.4 ± 1.1 | 0.002 |
| % NK1.1/DX5 | 16.4 ± 1.2 | 24.4 ± 3.3 | 0.032 | 2.5 ± 0.3 | 2.4 ± 0.2 | 0.862 |
| % CD19/B220 | 22.3 ± 0.5 | 8.4 ± 0.8 | 0.001 | 16.2 ± 1.3 | 8.6 ± 0.9 | 0.004 |

*Mann-Whitney U-Test

TABLE 2

Induction of CD11c positive cells in the spleen of 1-day-old wt mice and mice with gene-targeted disruptions within 7 days after MVA-treatment.

| Mouse strain | MVA dose (TCID$_{50}$) | controls % CD11c | MVA-BN % CD11c | ratio |
|---|---|---|---|---|
| wt[a] | $2.5 \times 10^7$ | 2.8 | 7.9 | 2.8 |
| Wt | $2.5 \times 10^6$ | 2.1 | 11.9 | 5.6 |
| Wt | $2.5 \times 10^5$ | 2.5 | 6.6 | 2.6 |
| RAG[b] | $2.5 \times 10^7$ | 4.2 | 5.4 | 1.3 |
| AG129[c] | $2.5 \times 10^3$ | 2.6 | 2.7 | 1.0 |

[a]Wt = either C57BL/6 or 129 Sv/Ev mice.
[b]RAG mice deletion in recombination activating gene (i.e no functional T and B cells).
[c]AG129 gene targeted disruptions of IFN receptor Type I (IFN-α and -β) and Type II (IFN-γ)

(ii) MVA-BN Induces Preferentially Plasmocytoid Dendritic Cells (pDC).

According to other authors, CD11c positive cells that also expressed CD45RA or CD45R were considered as pDC (Asselin-Paturel, et al. 2001, *Nat Immunol*, 12: 1144). It was asked whether MVA-BN induced an increase of pDC. A further experiment was performed in which CD45RA or CD45R on CD 11c positive cells were also analysed. The percentage of CD11c and CD45R double positive cells was Example 2

(i) MVA-BN Treated Neonatal Mice Survive a Challenge With 100 to 500 LD 50 of HSV-1

Figure 4:
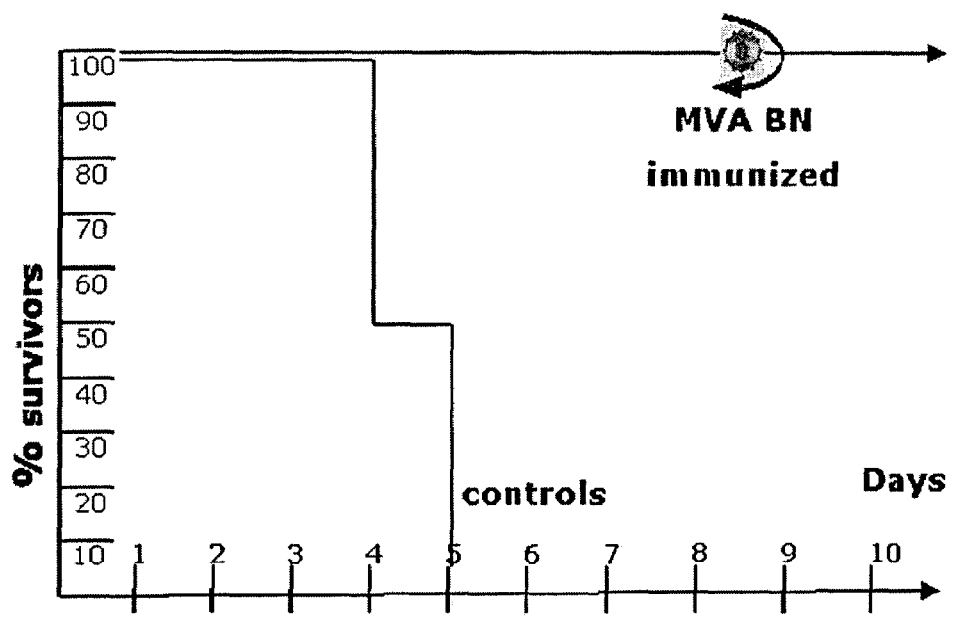

Groups of mice were treated with the standard dose of MVA-BN 1 or 2 days after birth, and challenged at 7 to 8 days of age with 100 to 500 LD 50 of Herpes simplex virus 1 (HSV-1) (FIG. 4). MVA BN treated mice survived the challenge with HSV 1, whereas all the control mice died within 5 to 6 days after inoculation with the challenge virus.

To further support these observations, 9 challenge experiments were performed with 40 MVA BN treated and 45 control mice. More than 80% of the virus treated mice survived the challenge, whereas all the control mice died (FIG. 5).

In a separate set of experiments, the mice were treated at birth with MVA-BN ($2.5 \times 10^6$ TCID$_{50}$/mouse). At day 8, a challenge with either $10^3$ (1 LD$_{50}$) or $10^5$ (100 LD$_{50}$) pfu of HSV-1 was performed. Following MVA-BN vaccination, 65% of the mice survived a viral dose that killed 100% of the control mice (100 LD$_{50}$), and 90% survived a dose that killed 45.5% of the controls (1 LD$_{50}$). In additional experiments, a group of 7 mice vaccinated with UV-inactivated MVA-BN were infected with HSV-1. Five of them died within 7 days. The remaining 2 animals ceased to grow and died at day 22 and 29. Therefore, mice treated with MVA-BN reached a state of increased resistance against HSV-1 that was associated with live MVA-BN, but not inactivated MVA-BN.

In control experiments done with mice that did not have functional T-cells, it was determined that the protection against HSV-1 after vaccination with MVA-BN was not due to cross-reacting cytotoxic T-lymphocytes induced by MVA-BN.

It was tested whether DC cells were responsible for the protection of mice from HSV-1 after vaccination with MVA-BN. To this end, naive 8-day-old mice were challenged with 5×10$^4$ PFU HSV-1 four hours after transfer of cells from MVA-treated mice. In a first experiment, splenocytes from 8-day-old mice treated at 1 day of life with MVA-BN were separated in DC rich (low-density) and DC poor (high-density) fractions. Up to 50% of the mice receiving 5×10$^6$ cells from the DC rich fraction survived the challenge; whereas, all the mice receiving 10 times less DC rich suspension, or untreated mice, died within 5 days. A second approach was done by transferring positively isolated CD11c positive cells from 8-day-old mice treated at 1 day of life with MVA-BN to naive age matched mice. A suspension of 2×10$^6$ splenocytes containing more than 80% CD11c positive cells from MVA-BN treated mice, protected naive mice from HSV-1 infection. In contrast, 4 untreated littermates, as well as, 8 additional untreated animals, died after the challenge. Furthermore, mice receiving the same amount of spleen cells, or mice receiving one spleen equivalent (50×10$^6$ cells) from the negative fraction, did not show increased resistance against HSV-1. Thus, CD11c positive cells are able to protect mice from HSV-1.

After administration of MVA, short-term protective effects in the range of about 24 hours were described in the prior art (Vilsmeier, B., Berl. Munch. Tierärztl. Wschr. 112 (1999), 329–333). Although, the viruses used in the publication are not viruses that are not capable of being replicated to infectious progeny virus in the neonatal or prenatal animal used; it was tested whether the mode of action as disclosed in Vilsmeier, is similar to the mode of action described in the present application. More particularly, Vilsmeier discloses that MVA, in particular inactivated MVA, induces a paramunity for about 24 hours. To test whether the paramunity effect accounts also for the protective effects as disclosed in the present application, mice 24 hours after birth were vaccinated either with MVA-BN or with inactivated MVA-BN. At 7 days of age, the mice were challenged with a lethal dose of HSV-1 (10$^5$PFU HSF-1f). Unvaccinated control mice died 6 days after challenge. Also, the mice vaccinated with inactivated MVA-BN were not protected against a challenge with HSV-1. The number of DC cells in these mice was not elevated. In contrast, the mice vaccinated with non-inactivated MVA-BN were significantly protected against a challenge with HSV-1. Thirty days after the challenge, more than 80% of the mice were still alive. Two days after vaccination, elevated serum levels of Flt3-L were found. In addition, elevated numbers of DC were found in the spleen. The enhanced Flt3-L was associated with elevated numbers of DC. This confirms that paramunity effects are not responsible for the observed protection.

(ii) MVA-BN Induces a Specific Immunity in Neonates That Lasts Until Adult Hood

One-day-old C57Bl/6 mice (group size of 18) were vaccinated (i.p) with MVA-BN (2.5×10$^7$ TCID$_{50}$). Four weeks after vaccination, when the mice were considered adults, they where challenged with a lethal dose (1×10$^4$ TCID$_{50}$) of vaccinia Western Reserve (VV-WR). With the exception of one animal, all other MVA-BN vaccinated animals survived. In contrast, all placebo vaccinated animals died within 7 days and demonstrated severe clinical symptoms such as ruffled fur, weight loss and reduced activity. This clearly demonstrates that MVA-BN vaccination is not only safe in neonatal animals, but is also capable of inducing a protective immune response against a lethal vaccinia (related virus to MVA-BN) infection.

The invention claimed is:

1. An MVA derived vaccinia virus characterized by
   (i) being capable of reproductive replication in chicken embryo fibroblasts (CEF) and the Baby hamster kidney cell line BHK but not capable of reproductive replication in the human cell line HaCaT, and
   (ii) by a failure to replicate in a mouse strain that is incapable of producing mature B and T cells and as such is severely immune compromised and highly susceptible to a replicating virus,
   wherein the virus induces a general immune stimulation and/or an immune response directed against foreign antigens and/or an immune response against antigens associated with the virus when administered to a neonatal animal, including a human.

2. The MVA derived vaccinia virus of claim 1, wherein the MVA derived vaccinia virus is MVA-BN deposited at the European Collection of Cell Cultures (ECACC), Salisbury (UK) under number V00083008 or derivatives thereof exhibiting the same replication characteristics.

3. The MVA derived vaccinia virus of claim 1, wherein the general immune stimulation is characterized by stimulating a general immune response not specific to the natural antigens associated with the virus.

4. The MVA derived vaccinia virus of claim 1, wherein the general immune stimulation is characterized by an increase in the number of dendritic cells and their precursor cells.

5. The MVA derived vaccinia virus of claim 4, wherein the precursors of dendritic cells are plasmacytoid dendritic cell precursors.

6. The MVA derived vaccinia virus of claim 1, wherein the general immune stimulation is characterized by an at least 1.5 fold increase in the concentration of Flt3-L two days after administration of the virus.

7. The MVA derived vaccinia virus of claim 1, wherein the virus comprises at least one heterologous nucleic acid sequence.

8. The MVA derived vaccinia virus of claim 7, wherein the heterologous nucleic acid sequence is selected from a sequence encoding at least one antigen, antigenic epitope, and/or a therapeutic compound.

9. The MVA derived vaccinia virus of claim 7, wherein the heterologous nucleic acid sequence encodes a foreign antigen.

10. The MVA derived vaccinia virus of claim 7, wherein the heterologous nucleic acid sequence encodes a protein selected from Interferon, IL-12, Flt-3L and GM-CSF.

11. The MVA derived vaccinia virus of claim 1, wherein the foreign antigen is different from the epitopes and antigens of the virus particle and the antigens and epitopes on the surface of a cell infected with the virus which are the result of the expression of the viral genome.

12. The MVA derived vaccinia virus of claim 11, wherein the foreign antigen is selected from infectious agents and toxins.

13. The MVA derived vaccinia virus of claim 12, wherein the infectious agent is selected from viruses, bacteria and fungi.

14. The MVA derived vaccinia virus of claim 13, wherein the infectious agent is a virus selected from herpesvirus, retrovirus, rabiesvirus, rhabdovirus and adenovirus.

15. The MVA derived vaccinia virus of claim 1, wherein the virus induces an immune response against antigens associated with the virus.

16. The MVA derived vaccinia virus of claim 15, wherein the virus induces an immune response against a poxvirus.

17. The MVA derived vaccinia virus of claim 16, wherein the virus induces an immune response against smallpox.

18. The MVA derived vaccinia virus of claim 8, wherein the virus induces an immune response against an agent from which the antigen and/or antigenic epitope encoded by the heterologous nucleic acid sequence is derived.

19. The MVA derived vaccinia virus of claim 9, wherein the virus induces an immune response against a toxin or an infectious agent from which the foreign antigen is derived.

20. The MVA derived vaccinia virus of claim 19, wherein the infectious agent is selected from bacteria, fungi and viruses other than MVA.

21. The MVA derived vaccinia virus of claim 20, wherein the viruses other than MVA are selected from HIV-1, HIV-2, Denguevirus, West-Nile-Virus, Japanese Encephalitis virus and measles virus.

22. A method of inducing a general immune stimulation and/or an immune response directed against foreign antigens and/or an immune response against antigens associated with the virus in a neonatal animal, including a human, comprising the administration of the MVA derived vaccinia virus of claim 1 to a neonatal animal, including a human.

23. The method of claim 22, wherein the MVA derived vaccinia virus is administered by oral, nasal, intramuscular, intravenous, intraperitoneal, intradermal, intra-utero and/or subcutaneous application.

24. The method of claim 22, wherein the MVA derived vaccinia virus is administered with a therapeutically effective amount in a first inoculation ("priming inoculation") and in a second inoculation ("boosting inoculation").

25. The method of claim 22, wherein the MVA derived vaccinia virus is administered to the neonatal animal, including a human, in an amount of at least $10^1$ $TCID_{50}$ (tissue culture infectious dose) of MVA.

26. The method of claim 22, wherein the general immune stimulation and/or an immune response directed against foreign antigens and/or an immune response against antigens associated with the virus is exerted for at least 14 days.

* * * * *

UNITED STATES PATENT AND TRADEMARK OFFICE
CERTIFICATE OF CORRECTION

| | | |
|---|---|---|
| PATENT NO. | : 7,097,842 B2 | Page 1 of 1 |
| APPLICATION NO. | : 10/418854 | |
| DATED | : August 29, 2006 | |
| INVENTOR(S) | : Mark Suter et al. | |

It is certified that error appears in the above-identified patent and that said Letters Patent is hereby corrected as shown below:

Column 5, Line 51:   "Orthopoxyirus" should be --Orthopxvirus--.

Column 5, Line 52:   "Poxyiridae" should be --Poxviridae--.

Column 9, Line 4:   "poxyiral" should be --poxviral--.

Column 9, Line 24:   "poxyiruses" should be --poxviruses--.

Column 9, Line 25:   "poxyirus" should be --poxvirus--.

Column 10, Line 28:   "poxyirus"should be --poxvirus--.

Column 10, Line 31:   "poxyirus" should be -- poxvirus--.

Column 17, Line 2:   "poxyirus" should be --poxvirus--.

Column 17, Line 4:   "poxyirus" should be --poxvirus--.

Column 18, Line 45:   "poxyirus" should be --poxvirus--.

Column 18, Line 46:   "poxyirus" should be --poxvirus--.

Column 18, Line 61:   "poxyirus" should be --poxvirus--.

Column 18, Line 62:   "poxyirus" should be --poxvirus--.

Signed and Sealed this

Twenty-eighth Day of November, 2006

JON W. DUDAS
*Director of the United States Patent and Trademark Office*